United States Patent
Racky

[11] Patent Number: 5,798,095
[45] Date of Patent: Aug. 25, 1998

[54] HAIR TREATMENT COMPOSITION AND METHOD OF MAKING SAME

[75] Inventor: Ernst Dieter Racky, Eppstein/Ts., Germany

[73] Assignee: Wella Aktiengesellschaft, Darmstadt, Germany

[21] Appl. No.: 648,342

[22] Filed: May 15, 1996

[30] Foreign Application Priority Data

Jul. 15, 1995 [DE] Germany .................. 195 25 821.5

[51] Int. Cl.⁶ ............................................. A61K 7/06
[52] U.S. Cl. ..................... 424/70.19; 424/70.21; 424/70.27; 424/70.28
[58] Field of Search ................ 424/70.1, 70.19, 424/70.21, 70.27, 70.28, 70.31; 510/119, 123, 124, 126, 275

[56] References Cited

U.S. PATENT DOCUMENTS

| | | | |
|---|---|---|---|
| 5,073,371 | 12/1991 | Turner et al. | 424/401 |
| 5,154,850 | 10/1992 | Deguchi et al. | 510/420 |
| 5,514,369 | 5/1996 | Salka et al. | 424/70.1 |
| 5,631,218 | 5/1997 | Allan et al. | 510/423 |
| 5,635,469 | 6/1997 | Fowler et al. | 510/406 |

FOREIGN PATENT DOCUMENTS 157750  9/1983  Japan.

OTHER PUBLICATIONS

Mehrfunktionelle N-Tenside pp. 328–332 (1992).

*Primary Examiner*—S. Mark Clardy
*Assistant Examiner*—Robert H. Harrison
*Attorney, Agent, or Firm*—Michael J. Striker

[57] ABSTRACT

The hair treatment composition is free of anionic surfactant, has a pH of from 2 to 7 and includes a combination of 0.5 to 15 percent by weight of a surfactant component A) consisting of at least one water-soluble cationic surfactant and/or at least one water-soluble amphoteric surfactant and 0.05 to 5 percent by weight of a component B) consisting of benzoic acid or its physiologically compatible salts or saccharin or its physiologically compatible salts of saccharin with inorganic bases or a mixture of a physiologically compatible salt of saccharin and a physiologically compatible salt of benzoic acid. A weight ratio of surfactant component A) to component B) is from 2:1 to 1:10. A room-temperature method of making the hair treatment composition is also described. The viscosity of the hair treatment composition can be adjusted without difficulty. It improves the wet and dry combability of hair and reduces the electrostatic charge on dry hair without loading the hair after several applications.

10 Claims, No Drawings

HAIR TREATMENT COMPOSITION AND METHOD OF MAKING SAME

BACKGROUND OF THE INVENTION

The present invention relates to a hair treatment composition and method of making it.

The subject matter of the invention is an anionic surfactant-free hair treatment composition based on a combination of at least one water-soluble cationic and/or at least one water-soluble amphoteric surfactant with benzoic acid or saccharin or their salts or with a combination of a salt of saccharin and a salt of benzoic acid as well as a process for making the composition at room temperature.

The physical, chemical and morphological properties of hair are negatively influenced by many different types of effects. The hair structure is thus damaged by cosmetic treatments, such as repeated bleaching, permanent waves and dyeing processes, but also by frequent washing of the hair with de-greasing surfactants and by climatic influences, such as moisture or temperature differences or the intensive action of sunlight. The hair becomes brittle and looses its shine. Hair damaged in this manner carries an electric charge due to combing and brushing and the roughened hair surface leads to poor combability of the hair and tangled hair because of matting and knotting. Hair treatment compositions which improve hair care and combability thus have achieved considerable importance.

Hair treatment compositions act to improve the condition of the hair and are usually in the form of emulsions, which contain fatty alcohol, waxes and oils as well as anionic and cationic surfactants. These hair treatment compositions can be made in emulsion form only with considerable energy and time consumption, because the fats contained in them must be emulsified by intensive mixing in a heated melted state. Providing the emulsion-form hair care composition with a user-friendly viscosity has proven to be difficult in the past. Particularly the final viscosity of fatty alcohol emulsions depends very greatly on the crystallization behavior of the fatty alcohol during the cooling process. Extreme viscosity variations result from different mixing and stirring speeds. If the dispersion becomes too thin, there is no possibility to increase the consistency in the cooled state, that is at room temperature. The mass must be warmed again to the melt temperature in order to cool under controlled conditions. Certain ingredients, which are usually added at lower temperature, such as perfume oil, are destroyed or volatilized.

Furthermore cold emulsifying succeeds with few emulsion-form hair treatment compositions. In this case the thickening compositions are continuously used to achieve the desired consistency.

In contrast, aqueous gels can be prepared without problem at room temperature. Usually hair treatment compositions in the form of aqueous gels have however a content of gel-forming polymers, which accumulate on the hair after several applications of the gel-form hair treatment composition. The residue of the gel-forming polymers left on the hair leads to a clear degradation of the wet and dry combability.

SUMMARY OF THE INVENTION

It is an object of the present invention to provide a hair treatment composition which can be made at room temperature, and which does not have the above-mentioned disadvantages of conventional emulsion-form or gel-form hair treatment compositions.

According to the invention the hair treatment composition is free of anionic surfactants and comprises a combination of A) 0.5 to 15 percent by weight of at least one water-soluble cationic and/or at least one water-soluble amphoteric surfactant; and B) 0.05 to 5 percent by weight of benzoic acid or its physiologically compatible salt or saccharin or its physiologically compatible salt with an inorganic base or a combination of a physiologically compatible salt of saccharin with an inorganic base and a physiologically compatible salt of benzoic acid;

wherein the weight ratio of component B) to component A) is from 2:1 to 1:10, preferably 1.5:1 to 1:5, and the pH-value of the composition is from 2 to 7.

The above-described hair treatment composition according to the invention attains the objects of the invention in an outstanding manner.

The hair treatment composition according to the invention can be made at room temperature, which means "cold" according to colloquial speech.

The term "room temperature" means a temperature in the temperature range of from 15° to 35° C., at which the composition can be prepared without addition of heat.

The adjustment of the viscosity of the composition to a predetermined viscosity is possible in the composition according to the invention by selection of suitable proportions or concentration ratios of both components A) and B). The gel-like hair treatment composition according to the invention improves the wet and dry combability of the hair and reduces the electrostatic charge on the hair, without loading the hair after several application cycles.

The viscosity of the composition according to the invention depends on the total concentration of components A) and B). The viscosity of the composition according to the invention can be between 1.1 to 5000 mPas, advantageously from 3 to 3000 mPas and especially between 10 to 2000 mPas, (millipascalseconds), at 25° C. and a shear rate of 50 $s^{-1}$. At higher concentrations of A) and B) a flow boundary can be formed between 0.01 to 10 Pascal, so that the composition has the flow properties of a plastic body.

The viscosity was measured with a Haake-rotating viscometer VT 501, measuring system MV-DIN, at a shear rate of 50 $s^{-1}$ and at 25° C.

Those cationic or amphoteric surfactants are suitable as water-soluble surfactants for component A), which are clearly water-soluble at a pH-value of 2 to 7 and a surfactant concentration of 15 percent by weight and present completely or at least partially in cationic form.

The water-soluble cationic surfactant of component A) is advantageously selected from the group consisting of the $C_{12}$- to $C_{18}$-alkyl pyridinium chlorides and bromides and quaternary ammonium compounds of formula (I):

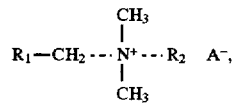

wherein $R_1$ represents a $C_7$- to $C_{15}$-alkyl group, a $C_{11}$- to $C_{17}$-alkoxy carbonyl group or a $C_8$- to $C_{16}$-alkylcarboxylmethyl group, when $R_2$ represents a methyl group, and wherein $R_1$ represents a $C_7$- to $C_{15}$-alkyl group, when $R_2$ represents a benzyl group, a polyethylene glycol group or a polypropylene glycol group, which is alkoxylated with up to 5 Mol ethylene oxide or propylene oxide units, and wherein A⁻ represents a chloride, bromide, sulfate, hydrogen sulfate, hydrogen phosphate, lactate, citrate or methosulfate anion.

The water-soluble cationic surfactant is preferably a betaine ester of a $C_{10}$- to $C_{16}$-fatty alcohol of the formula (II):

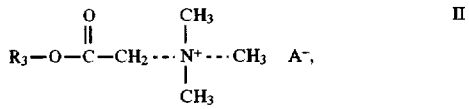

wherein $R_3$ represents a $C_{10}$- to $C_{16}$-alkyl group and A⁻ represents a chloride, bromide, sulfate, hydrogen sulfate, hydrogen phosphate, lactate, citrate or methosulfate anion, and particularly $R_3$ represents preferably a cetyl group or lauryl group and A⁻ represents preferably a chloride or bromide anion.

The betaine ester of a $C_{10}$- to $C_{16}$-fatty alcohol can be made according to the synthesis described in the published Japanese Patent Application 157 750 of 1983.

Cationic surfactants suitable as component A) are, for example, cetyltrimethyl ammonium chloride, which is obtainable in the form of the commercially available product Arquad® 16–25 of Akzo Chem. GmbH, Düren, Germany; lauryl dimethyl benzyl ammonium chloride, which can be purchased, for example, from the firm Henkel KGaA, Düsseldorf, Germany in the form of a powder as the commercially available product, Dehyquart® C; and lauryl dimethyl benzyl ammonium chloride, which is marketed under the Trademark Dehyquart® LDB in the form of a 35 percent aqueous solution from Henkel KGaA.

Aqueous solutions of $C_8$- to $C_{16}$-fatty acid esters of cholines, which are designated also as monoesterquats and which, for example, are made by a synthesis from choline chloride and fatty acid chlorides which is described in Tensid Surf. Det. 29 (5), 1992, pp. 328 to 332, are suitable as component A) in the composition according to the invention.

The amphoteric surfactant of component A) is preferably at least one member of the group consisting of carboxyl derivatives of imidazoles and $C_8$- to $C_{16}$-N-alkyl betaines.

As component A) the following water-soluble amphoteric surfactants are suitable, for example, lauryldimethylglycine, which is marketed in the form of a 15 percent aqueous solution under the Trademark Rewoteric® AM DL of the firm Rewo Chem. Werke Steinau, Germany; coconut oil alkyldimethylaminoacetic acid betaine (CFTA-tradename—Coco-betaine), which is marketed under the Trademark Dehyton® AB 30 in the form of a 30 percent aqueous solution by the firm Henkel KGaA, Düsseldorf, Germany; the sodium salt of 1-(carboxymethyl)-4,5-dihydro-1-(2-hydroxyethyl)-2-undecyl-1H-imidazolium hydroxide (CFTA-tradename sodium lauroamphoacetate), which is commercially available under the Trademark Miranol® HM conc. in the form of a 37 percent aqueous solution from the firm Miranol Chem. Company Inc., South Brunswick, U.S.A.; lauryldimethyl glycine (CFTA-tradename: lauryl betaine), which is marketed under the trademark Empigen® BB of the firm Albright & Wilson Ltd., Whitehaven, Great Britain and under the trademark Armoteric® by the firm Akzo Chemie, Düren, Germany in the form of a 30 percent aqueous solution and by the firm Rewo Chemical Works GmbH in the form of a 39 percent aqueous solution.

The composition according to the invention preferably contains from 0.5 to 5.0 percent by weight, particularly preferably from 0.5 to 2 percent by weight, of component A).

Salts of benzoic acid suitable as component B) are preferably sodium benzoate, potassium benzoate, magnesium benzoate or ammonium benzoate. Salts of saccharin which are suitable as component B) include sodium saccharinate, potassium saccharinate and ammonium saccharinate. Sodium saccharinate is preferred among the salts of saccharin with inorganic bases as component B).

Sodium benzoate and/or sodium saccharinate are particularly preferred as component B) in the composition according to the invention.

Component B) is advantageously present in the composition according to the invention in an amount of from 0.5 to 5 percent by weight.

The water content of the hair treatment composition according to the invention advantageously amounts to from 80 to 99 percent by weight.

The pH of the composition according to the invention is preferably between 2 and 6, especially preferably between 3 and 6. It can be adjusted with physiologically compatible inorganic or organic salts, especially with acetic acid, lactic acid, citric acid, hydrochloric acid or betaine hydrochloride.

In a special embodiment the composition according to the invention can also contain in addition to the combination of components A) and B) from 0.01 to 10 percent by weight of a water-soluble, mono- or polyvalent alcohol or a water-soluble physiologically compatible, univalent metal salt of an inorganic or organic acid as an additional component C). However the weight percentage of component C) in the composition according to the invention is at most equal to half the sum of the weight percentages of components A) and B).

Salts suitable as component C) are especially sodium chloride, potassium chloride, calcium chloride, sodium sulfate, magnesium sulfate, sodium citrate, sodium hydrogen sulfate and sodium salts of phosphoric acid.

The water-soluble univalent or polyvalent alcohols suitable for component C) are especially those selected from the group consisting of lower polyglycols, such as 1,2-propyleneglycol; isopropanol, ethanol, glycerol, pentaerythritol and polyglycerols.

The component C) can be added to the composition according to the invention for fine adjustment of a predetermined viscosity.

In a special embodiment of the composition according to the invention it can contain 0.05 to 2.0 percent by weight of at least one direct dyeing hair dye for simultaneous dyeing of the hair, which can be selected from the following classes of direct dyeing hair dyes: aromatic nitrodyes, e.g. 2-[(4-amino-3-nitrophenyl)amino]ethanol (HC Red No. 7), 2-[2-amino-4-nitrophenyl)amino]ethanol (HC Yellow No.5), 1,4-diamino-2-nitrobenzene and 1-hydroxy-2-amino-nitrobenzene; azodyes, e.g. Basic Brown 16 (C.I. 12 250), Acid Brown 4 (C.I. 14 805); aminoketones, such as 3-[(4-amino-6-bromo-5-oxo-2-naphthalenyl)amino]-N,N,N-trimethylbenzaminium chloride (Basic Blue 99, C.I. 56 059); anthraquinone dyes, e.g. 1-amino-4-aminoethylanthraquinone, Disperse Violet 4 (C.I. 61 105) and triphenylmethane dyes, e.g. Basic Violet 1 (C.I. 42 535), in which the dye compounds, according to their substituents, can have acidic, nonionogenic or basic character. This special embodiment of the composition according to the invention acting as a hair tinting agent has advantageously a viscosity of from 13 to 1390 mPas.

In an additional embodiment the composition according to the invention is a permanent wave hair fixing agent and contains an oxidizing agent, such as hydrogen peroxide, sodium and potassium bromate, sodium perborate or urea peroxide.

The concentration of the oxidizing agent differs according to the application time (usually about 5 to 15 minutes) and the application temperature; usually it is in a concentration range of from about 0.5 to 10 percent by weight. The permanent wave fixing composition can understandably contain other materials, such as wetting agents, weak acids, buffer substances or peroxide stabilizers.

In addition to the combination of the components A) and B) the hair treatment composition according to the invention can contain all those ingredients which are commonly used in hair treatment compositions, especially nonionic surface active compounds (surfactants), e.g. fatty acid alkanol amides, ethoxylated sorbitan fatty acid ester, in an amount of 0.1 to 10 percent by weight, advantageously 0.5 to 2.5 percent by weight; pigments, perfume oils in an amount of from 0.5 to 5.0 percent by weight; turbidity inducing agents, such as ethyleneglycol distearate, in an amount of about 0.5 to 5.0 percent by weight; pearlescent agents, such as a mixture of fatty acid monoalkylol amide and ethyleneglycol distearate, in an amount of about 1.0 to 10.0 percent by weight; buffer substances such as sodium citrate or sodium phosphate, in an amount of from about 0.1 to 1.0 percent by weight; solubilizing agents, such as ethoxylated, as required hydrogenated, castor oil, in an amount of about 0.1 to 1.0 percent by weight; and dye compounds, such as fluorescein sodium salt, in an amount of about 0.1 to 1.0 percent by weight; additional hair care additives, such as fatty acid esters, fatty alcohols, cationic modified natural or cationic synthetic polymers, such as cationic cellulose derivatives or cationic chitin derivatives; hair care materials, such as lanolin derivatives, cholesterol and pantothenic acid, in an amount of about 0.1 to 10 percent by weight; furthermore physiologically compatible inorganic salts, such as calcium chloride or magnesium sulfate and moisturizing agents; plant extracts; protein hydrolyzates; dyeing materials; light protective agents; anti-oxidants; complex formers; anti-flaking agents; cosmetic oils and waxes and preservative materials.

The composition according to the invention can contain up to 0.5 percent by weight of gel-forming natural or synthetic polymers but is however preferably free of natural or synthetic polymers. The composition according to the invention can be present in the form of a suspension, emulsion or a gel and can contain the conventional cosmetic additives for hair treatment composition preferably in an amount of 0.01 to 20 percent by weight.

The composition according to the invention can be present in the form of a non-aerosol foam or in the form of a sprayed hair treatment composition which is sprayed with the help of a suitable mechanically operated spray apparatus. Mechanical spraying apparatuses are those which permit the spraying of a liquid without using a liquified propellant. For example spray pumps or elastic containers provided with suitable spraying valves, in which the cosmetic composition according to the invention can be filled under pressure, can be used as mechanical spraying apparatuses according to the invention. The elastic container expands as it is filled under pressure and the composition according to the invention is continuously discharged from the elastic container due to contraction when the spray valve is opened.

The composition according to the invention can also be filled in a pressurized container pressurized by addition of a propellant. The preparation is released as a foam, easily metered by means of a valve provided with an application nozzle and conveniently distributed on the hair. Lower alkanes, e.g. n-butane, butane, i-butane and propane are suitable as propellants or also dimethyl ether and further pressurized gaseous propellants, such as $N_2$, $N_2O$ and $CO_2$ and mixtures of the aforementioned compounds. The propellants are contained in the compositions suitably in an amount of from about 2 to 10 percent.

The composition according to the invention is preferably a hair care composition and can be present as a Leave-in-Conditioner, as a care foam, as a hair rinse and as a care pack.

The compositions according to the invention, which are rinsed out after use, such as a hair care agent and a hair rinse, are usually applied to hand-towel dried hair in an amount of about 10 to 30 g according to the hair amount after washing the hair. After an acting time of 1 to 30 minutes, advantageously 3 to 15 minutes, the hair is rinsed with water and then dried.

The particular acting time of the composition according to the invention within the stated time limits depends on its purpose. The composition is left on the hair from 1 to 5 minutes in the case of a hair rinse, while an acting time of from 3 to 15 minutes is used in the case of a hair care composition and an acting time of 10 to 30 minutes is used for a hair care composition which simultaneously dyes the hair.

The compositions according to the invention, which are again not rinsed from the hair, such as the Leave-in-Conditioner, are distributed in hand towel dried hair in an amount of from 2 to 4 g according to the hair amount.

The process for making the hair treatment composition according to the invention is also the subject matter of the present invention. The process according to the invention for making the hair treatment composition comprises dissolving component A) in from 50 to 90 percent of the total water amount used in the composition at room temperature and then mixing the component B) in the remaining 10 to 50 percent of the total water amount at room temperature.

If necessary the conventional cosmetic additives are added to the aqueous solution containing component A) prior to mixing with the solution containing component B).

When the composition according to the invention is to contain the component C) in the previously described special embodiment in addition to the combination of components A) and B), during the making of that embodiment of the composition the component C) is added after mixing of the aqueous solutions of components A) and B). If necessary the aqueous solution of component A) contains cosmetic additives for the hair treatment composition.

Hair treated with the compositions according to the invention has an outstanding wet and dry combability, a pleasant feel and a pleasing shine in the dry state.

The following examples should illustrate the subject matter of the invention in greater detail.

EXAMPLES

Examples 1 to 5

Hair Treatment Compositions According to the Invention

| Example | 1 | 2 | 3 | 4 | 5 |
|---|---|---|---|---|---|
| betaine lauryl ester | 3.20 g | 3.20 g | 6.40 g | — | — |
| betaine cetyl ester | — | — | — | 3.80 g | 3.80 g |
| sodium benzoate | — | — | — | 1.20 g | 1.20 g |
| sodium saccharinate dihydrate | 1.60 g | 2.00 g | 3.20 g | — | — |
| 1,2-propylene glycol | — | — | — | — | 1.00 g |
| citric acid monohydrate | 0.10 g | 0.10 g | 0.10 g | 0.10 g | 0.10 g |
| water | 95.10 g | 94.70 g | 90.30 g | 94.90 g | 94.95 g |
|  | 100.00 g | 100.00 g | 100.00 g | 100.00 g | 100.00 g |
| Viscosity [mPas] (25° C./ 50 s$^{-1}$) | 16.0 | 19.0 | 73.0 | 640 | 420 |

Examples 6 to 10

Hair Treatment Compositions According to the Invention

| Example | 6 | 7 | 8 | 9 | 10 |
|---|---|---|---|---|---|
| cetyltrimethyl ammonium chloride | 1.60 g | 1.60 g | 2.50 g | 5.00 g | 8.80 g |
| sodium benzoate | 0.70 g | 0.70 g | 1.20 g | 2.20 g | 4.10 g |
| sodium chloride | — | 1.00 g | — | — | — |
| citric acid monohydrate | 0.05 g | 0.05 g | 0.30 g | 0.30 g | 0.30 g |
| water | 97.65 g | 97.65 g | 96.00 g | 92.50 g | 86.80 g |
|  | 100.00 g | 100.00 g | 100.00 g | 100.00 g | 100.00 g |
| Viscosity [mPas] (25° C./ 50 s$^{-1}$) | 3.0 | 4.0 | 15.0 | 550 | 2600 |

Example 11

Hair Dyeing Composition

| | |
|---|---|
| 1.25 g | cetyltrimethylammonium chloride |
| 0.50 g | sodium benzoate |
| 0.75 g | sodium saccharinate |
| 0.01 g | citric acid |
| 0.70 g | 2-[(4-amino-3-nitrophenyl)amino]ethanol |
| 0.25 g | 2-[(2-amino-4-nitrophenyl)amino]ethanol |
| 0.05 g | 3-[(4-amino-6-bromo-5-oxo-2-naphthalenyl)amino]-N,N,N-trimethylbenzaminium chloride (C.I. 56 059) |
| 96.49 g | water |
| 100.00 g | |

The hair dyeing composition according to example 11 has a viscosity of 13.3 mPas at 25° C. and a shear rate of 50 s$^{-1}$. The hair treated with the hair dyeing composition according to example 11 has a warm red-brown shade.

Example 12

Hair Dyeing Composition

| | |
|---|---|
| 10.00 g | cetyltrimethylammonium chloride |
| 2.00 g | sodium saccharinate |
| 0.02 g | citric acid |
| 0.70 g | 2-[(4-amino-3-nitrophenyl)amino]ethanol |
| 0.25 g | 2-[(2-amino-4-nitrophenyl)amino]ethanol |
| 0.05 g | 3-[(4-amino-6-bromo-5-oxo-2-naphthalenyl)amino]-N,N,N-trimethylbenzaminium chloride (C.I. 56 059) |
| 86.98 g | water |
| 100.00 g | |

The hair dyeing composition according to example 12 has a viscosity of 1390 mPas at 25° C. and a shear rate of 50 s$^{-1}$. The hair treated with the hair dyeing composition according to example 12 has a warm red-brown shade.

Example 13

Hair Dyeing Composition

| | |
|---|---|
| 1.00 g | cetyltrimethylammonium chloride |
| 0.50 g | sodium benzoate |
| 0.50 g | sodium saccharinate |
| 0.01 g | citric acid |
| 0.15 g | 3-[(4-amino-6-bromo-5-oxo-2-naphthalenyl)-amino]-N,N,N-trimethylbenzaminium chloride (C.I. 56 059) |
| 0.03 g | [8-[(p-aminophenyl)azo]-7-hydroxy-2-naphthyl]-trimethylammonium chloride(Basic Brown 16, C.I. 12 250) |
| 0.20 g | 1-amino-4-aminoethylanthraquinone (C.I. 61 105) |
| 0.15 g | 2,2'-{4-(2-hydroxyethyl)amino-3-nitro-phenyl}imino-bis-ethanol |
| 97.46 g | water |
| 100.0 g | |

The hair dyeing composition according to example 13 has a viscosity of 69.3 mPas at 25° C. and a shear rate of 50 s$^{-1}$ and hair treated with it has a violet-blue-gray color.

Example 14

Hair Dyeing Composition

| | |
|---|---|
| 2.50 g | cetyltrimethyl ammonium chloride |
| 0.50 g | sodium benzoate |
| 2.00 g | sodium saccharinate |
| 0.02 g | citric acid |
| 0.15 g | 3-[(4-amino-6-bromo-5-oxo-2-naphthalenyl)-amino]-N,N,N-trimethylbenzaminium chloride (C.I. 56 059) |
| 0.03 g | [8-[(p-aminophenyl)azo]-7-hydroxy-2-naphthyl]-trimethyl ammonium chloride(Basic Brown 16, C.I. 12 250) |
| 0.20 g | 1-amino-4-aminoethylanthraquinone (C.I. 61 105) |
| 0.15 g | 2,2'-{4-(2-hydroxyethyl)amino-3-nitro-phenyl}imino-bis-ethanol |
| 94.45 g | water |
| 100.0 g | |

The hair dyeing composition according to example 14 has a viscosity of 229 mPas at 25° C. and a shear rate of 50 s$^{-1}$ and hair treated with it has a violet-blue-gray color.

Comparative Examples 15 to 17

Permanent Wave Fixing Composition

The viscosity of the composition of example 15 which is prepared according to the invention is compared with the viscosities of the compositions of examples 16 and 17 which are not according to the invention.

| Example 1 | 15 | 16 | 17 |
|---|---|---|---|
| lauryldimethylglycine | 4.50 g | 4.50 g | — |
| sodium salt of 1-(carboxymethyl)-4,5-dihydro-1-(2-hydroxyethyl)-2-unidecyl-1H-imidozolium hydroxide | 0.50 g | 0.50 g | — |
| sodium saccharinate | 2.00 g | — | 2.00 g |
| phenacetin | 0.04 g | 0.04 g | 0.04 g |
| polydimethyldiallyl ammonium chloride | 0.40 g | 0.40 g | 0.40 g |
| phosphoric acid, 85% | 0.50 g | 0.50 g | 0.50 g |
| hydrogen peroxide, 50% solution | 5.00 g | 5.00 g | 5.00 g |
| ethylenediamine tetracetic acid | 0.20 g | 0.20 g | 0.20 g |
| water | 86.86 g | 86.86 g | 91.86 g |
| | 100.00 g | 100.00 g | 100.00 g |
| pH-value | 3.6 | 3.5 | 2.3 |
| Viscosity [mPas] (25° C./ 50 s$^{-1}$) | 13.0 | 2 | 2 |

The permanent wave fixing composition according to example 15 is clear and viscous, while the compositions of examples 16 and 17 flow freely, i.e. are not viscous and are thin, and example 17 is a flocculent white dispersion.

Examples 18 to 21

Hair Treatment Composition

| Example | 18 | 19 | 20 | 21 |
|---|---|---|---|---|
| coconut oil alkyl dimethylaminoacetic acid betaine | 10.00 g | 10.00 g | 10.00 g | 10.00 g |
| sodium saccharinate | 1.67 g | 3.33 g | 1.00 g | 2.00 g |
| water | 88.33 g | 86.67 g | 93.00 g | 92.00 g |
| | 100.00 g | 100.00 g | 100.00 g | 100.00 g |

The pH-values of examples 18 to 21 were adjusted with hydrochloric acid to a pH value of 2.4.

| Viscosity [mPas] (25° C./ 50 s$^{-1}$) | 41 | 100 | 12 | 49.6 |
|---|---|---|---|---|

Examples 22 to 25

Hair Treatment Composition

| Example | 22 | 23 | 24 | 25 |
|---|---|---|---|---|
| lauryldimethyl glycine | 10.00 g | 10.00 g | 6.00 g | 6.00 g |
| sodium saccharinate | 2.50 g | 3.00 g | 3.50 g | 5.00 g |
| water | 87.50 g | 87.00 g | 86.50 g | 85.00 g |
|  | 100.00 g | 100.00 g | 100.00 g | 100.00 g |

The pH-values of examples 22 to 25 were adjusted with hydrochloric acid to a pH value of 3.9.

| Viscosity [mPas] (25° C./ 50 s$^{-1}$) | 18 | 34 | 50 | 81 |
|---|---|---|---|---|

Examples 26 and 27

Clear Care Rinse

| Example | 26 | 27 |
|---|---|---|
| cetyltrimethyl ammonium chloride | 1.00 g | 1.00 g |
| sodium saccharinate | 0.75 g | 0.75 g |
| citric acid | 0.20 g | 0.20 g |
| Plant Extract (Extapone 5 Special$^R$ of the firm Dragoco, Holzminden, Germany) | 0.20 g | 0.20 g |
| Dipalmitoylethylhydroxyethyl-methylammonium methosulfate | — | 0.05 g |
| Acid Yellow 3 (C.I; 47 065) | 0.13 g | 0.13 g |
| Pigment Green 7 (C.I. 74260) | 0.07 g | 0.07 g |
| Perfume | 0.10 g | 0.10 g |
| Water | 97.55 g | 97.50 g |
|  | 100.00 g | 100.00 g |
| pH-value | 2.7 | 2.6 |
| Viscosity [mPas] (25° C./ 50 s$^{-1}$) | 197 | 125 |

Examples 28 and 30

Clear Care Rinse

| Example | 28 | 29 | 30 |
|---|---|---|---|
| cetyltrimethyl ammonium chloride | 0.83 g | 0.83 g | 0.83 g |
| sodium saccharinate | 0.67 g | 0.67 g | 0.67 g |
| protein hydrolyzate (Nutrilan$^R$ of the firm Henkel, Düsseldorf, Germany) | 2.00 g | — | — |
| soja protein hydrolyzate | — | 0.50 g | — |
| collagen partial hydrolyzate (Croquat Soya$^R$ of Croda) (Gelita-Sol C$^R$ of the firm Deutsche Gelatine-Fabriken Stoess & Co. GmbH, Eberbach, Germany) | — | — | 1.00 g |
| lactic acid | 0.07 g | 0.07 g | 0.07 g |
| Acid Yellow 3 (C.I. 47 005) | 0.09 g | 0.09 g | 0.09 g |
| Pigment Green 7 (C.I. 74 260) | 0.05 g | 0.05 g | 0.05 g |
| Perfume | 0.10 g | 0.05 g | 0.04 g |
| Water | 96.19 g | 97.74 g | 97.25 |
|  | 100.00 g | 100.00 g | 100.00 g |
| pH-value | 4.1 | 3.5 | 4.0 |
| Viscosity [mPas] (25° C./ 50 s$^{-1}$) | 90 | 98 | 135 |

Examples 31 and 32

Turbid Clear Rinse

| Example | 31 | 32 |
|---|---|---|
| cetyltrimethyl ammonium chloride | 0.83 g | 0.83 g |
| sodium saccharinate | 0.67 g | 0.67 g |
| Stearyl alcohol | 1.00 g | — |
| Titanium(IV) oxide | — | 0.50 g |
| lactic acid | 0.50 g | 0.50 g |
| Acid Yellow 3 (C.I. 47 005) | 0.05 g | — |
| Pigment Green 7 (C.I. 74 260) | 0.15 g | — |
| Perfume | 0.10 g | 0.05 g |
| Water | 96.70 g | 97.45 g |
|  | 100.00 g | 100.00 g |
| pH-value | 4.1 | 3.2 |
| Viscosity [mPas] (25° C./ 50 s$^{-1}$) | 114 | 166 |

Examples 33 and 34

Rinse Composition

| Example | 33 | 34 |
|---|---|---|
| betaine lauryl ester chloride | 0.80 g | 0.80 g |
| sodium saccharinate | 0.65 g | 0.65 g |
| coconutmonoethanol amide | 5.00 g | — |
| coconutdiethanol amide | — | 5.00 g |
| lactic acid | 0.40 g | 0.40 g |
| Acid Yellow 3 (C.I. 47 005) | 0.05 g | 0.05 g |
| Pigment Green 7 (C.I. 74 260) | 0.15 g | 0.15 g |
| Perfume | 0.10 g | 0.08 g |

-continued

| Example | 33 | 34 |
|---|---|---|
| Water | 92.85 g | 92.87 g |
| | 100.00 g | 100.00 g |
| pH-value | 4.6 | 4.3 |
| Viscosity [mPas] (25° C./ 50 s$^{-1}$) | 113 | 76 |

All percentages, in this disclosure, unless stated otherwise, are percentages by weight.

While the invention has been illustrated and described as embodied in a hair treatment composition and method of making same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A hair treatment composition not containing any anionic surfactant, having a pH of from 2 to 7 and comprising a combination of from 0.5 to 15 percent by weight of at least one surface active component selected from the group consisting of water-soluble cationic surfactants and water-soluble amphoteric surfactants and from 0.05 to 5 percent by weight of a member selected from the group consisting of benzoic acid, physiologically compatible salts of benzoic acid, saccharin, physiologically compatible salts of saccharin with inorganic bases and combinations of the physiologically compatible salts of said saccharin with the physiologically compatible salts of said benzoic acid;

wherein a weight ratio of said member to said at least one surface active component is from 2:1 to 1:10.

2. The hair treatment composition as defined in claim 1, wherein said cationic surfactants are selected from the group consisting of $C_{12}$- to $C_{18}$-alkyl pyridinium chlorides, $C_{12}$- to $C_{18}$-alkyl pyridinium bromides and quaternary ammonium compounds of formula (I):

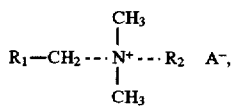

wherein $R_1$ is selected from the group consisting of $C_7$- to $C_{15}$-alkyl groups, $C_{11}$- to $C_{17}$-alkoxycarbonyl groups and $C_8$- to $C_{16}$-alkylcarboxylmethyl groups, when $R_2$ represents a methyl group, and wherein $R_1$ is selected from the group consisting of said $C_7$- to $C_{15}$-alkyl groups, when $R_2$ is selected from the group consisting of a benzyl group, polyethylene glycol groups ethoxylated with up to 5 Mol ethylene oxide, polyethylene glycol groups propyloxylated with up to 5 Mol propylene oxide, polypropylene glycol groups ethoxylated with up to 5 Mol ethylene oxide and polypropylene glycol groups propyloxylated with up to 5 Mol propylene oxide, and wherein $A^-$ is selected from the group consisting of a chloride anion, a bromide anion, a sulfate anion, a hydrogen sulfate anion, a hydrogen phosphate anion, a lactate anion, a citrate anion and a methosulfate anion.

3. The hair treatment composition as defined in claim 1, wherein said cationic surfactants are betaine esters of $C_{10}$- to $C_{16}$-fatty alcohols of the formula (II):

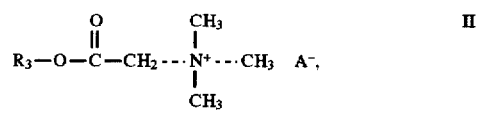

wherein $R_3$ represents a $C_{10}$- to $C_{16}$-alkyl group and $A^-$ is selected from the group consisting of a chloride, bromide, sulfate, hydrogen sulfate, hydrogen phosphate, lactate, citrate and methosulfate anion.

4. The hair treatment composition as defined in claim 1, wherein the amphoteric surfactants are selected from the group consisting of $C_8$- to $C_{16}$-N-alkyl betaines and carboxyl-substituted imidazoles having an imidazole ring with a 1-position and a 2-position with a carboxyl substituent on the 1-position and an alkyl group on the 2-position.

5. The hair treatment composition as defined in claim 1, further comprising an additional component consisting of 0.01 to 10 percent by weight of an ingredient selected from the group consisting of water-soluble one to pentavalent alcohols, water-soluble physiologically compatible univalent metal salts of inorganic acids and water-soluble physiologically compatible univalent metal salts of organic acids, wherein a weight proportion of said additional component is at most half of a sum of a weight proportion of said at least one surface active component and a weight proportion of said member.

6. The hair treatment composition consisting of 3.80 g of betaine cetyl ester, 1.20 g of sodium benzoate, 1.00 g of 1,2-propylene glycol, 0.10 g citric acid monohydrate and 94.95 g of water.

7. A hair treatment composition not containing any anionic surfactant, having a pH of from 2 to 7 and comprising a combination of:

from 0.5 to 15 percent by weight of betaine cetyl ester, from 0.05 to 5 percent by weight of sodium benzoate, 1,2-propylene glycol, citric acid monohydrate, and water;

wherein a weight ratio of said sodium benzoate to said betaine cetyl ester is from 2:1 to 1:10.

8. The hair treatment composition as defined in claim 7, containing from 80 to 99 percent by weight of said water.

9. The hair treatment composition as defined in claim 7, wherein said pH is from 3 to 6.

10. A hair treatment composition not containing any anionic surfactant, having a pH of from 2 to 7 and comprising a combination of:

from 0.5 to 15 percent by weight of at least one surfactant ingredient selected from the group consisting of water-soluble $C_{12}$- to $C_{18}$-alkyl pyridinium chlorides;
water-soluble $C_{12}$- to $C_{18}$-alkyl pyridinium bromides;
quaternary ammonium compounds of formula (I):

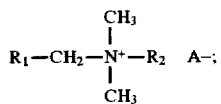

betaine esters of $C_{10}$- to $C_{16}$-fatty alcohols of the formula (II):

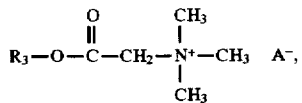

$C_8$- to $C_{16}$-N-alkyl betaines; and carboxyl-substituted imidazoles having an imidazole ring with a 1-position and a 2-position with a carboxyl substituent on the 1-position and an alkyl group on the 2-position;

wherein $R_1$ is a $C_7$- to $C_{15}$-alkyl group, a $C_{11}$- to $C_{17}$-alkoxycarbonyl group or a $C_8$- to $C_{16}$-alkylcarboxylmethyl groups, when $R_2$ represents a methyl group, and wherein $R_1$ is a $C_7$- to $C_{15}$-alkyl group, when $R_2$ is a benzyl group, a polyethylene glycol group ethoxylated with up to 5 Mol ethylene oxide, a polyethylene glycol group propyloxylated with up to 5 Mol propylene oxide, a polypropylene glycol group ethoxylated with up to 5 Mol ethylene oxide and a polypropylene glycol group propyloxylated with up to 5 Mol propylene oxide;

$R_3$ represents a $C_{10}$- to $C_{16}$-alkyl group and A– is a chloride, bromide, sulfate, hydrogen sulfate, hydrogen phosphate, lactate, citrate or a methosulfate anion; and from 0.05 to 5 percent by weight of a member selected from the group consisting of benzoic acid, physiologically compatible salts of benzoic acid, saccharin, physiologically compatible salts of saccharin with inorganic bases and combinations of the physiologically compatible salts of said saccharin with the physiologically compatible salts of said benzoic acid;

wherein a weight ratio of said member to said at least one surface active component is from 2:1 to 1:10.

* * * * *